(12) United States Patent
Kobayashi

(10) Patent No.: US 10,552,965 B1
(45) Date of Patent: Feb. 4, 2020

(54) ATOMIC ABSORPTION SPECTROPHOTOMETER

(71) Applicant: Shimadzu Corporation, Kyoto (JP)

(72) Inventor: Osuke Kobayashi, Kyoto (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 0 days.

(21) Appl. No.: 16/199,143

(22) Filed: Nov. 24, 2018

(51) Int. Cl.
| | | |
|---|---|---|
| *G01J 3/30* | (2006.01) | |
| *G06T 7/246* | (2017.01) | |
| *G06T 1/00* | (2006.01) | |
| *H04N 5/232* | (2006.01) | |
| *G01N 21/01* | (2006.01) | |
| *G01N 21/74* | (2006.01) | |

(52) U.S. Cl.
CPC ............. *G06T 7/248* (2017.01); *G01N 21/01* (2013.01); *G01N 21/74* (2013.01); *G06T 1/0007* (2013.01); *H04N 5/23299* (2018.08); *G01N 2021/745* (2013.01); *G06T 2207/30172* (2013.01)

(58) Field of Classification Search
CPC .................. G06T 7/248; G06T 1/0007; G06T 2207/30172; H04N 5/23299; G01N 21/01; G01N 21/74; G01N 21/62; G01N 2021/745; G01J 3/443
USPC .................................................. 356/311, 312
See application file for complete search history.

(56) References Cited

U.S. PATENT DOCUMENTS

| | | | | |
|---|---|---|---|---|
| 4,022,530 A | * | 5/1977 | Braun | ..................... G01N 21/74 356/244 |
| 4,204,770 A | * | 5/1980 | Tomoff | .................. G01N 21/74 356/244 |
| 2004/0223153 A1 | | 11/2004 | Sakai et al. | |
| 2017/0108450 A1 | * | 4/2017 | von Chamier-Glisczinski | ............ G01N 21/3103 |

FOREIGN PATENT DOCUMENTS

JP          2004-325341 A          11/2004

* cited by examiner

*Primary Examiner* — Tarifur R Chowdhury
*Assistant Examiner* — Jonathon Cook
(74) *Attorney, Agent, or Firm* — Muir Patent Law, PLLC

(57) ABSTRACT

The atomic absorption spectrophotometer is provided with an atomization unit, a light source, a detector, an optical system, a camera, and a captured image data storage unit. The atomization unit has a tube-like furnace and atomizes the sample injected into the furnace by heating the sample. The light source emits light of a wavelength of a measurement target toward the atomization unit so that the light passes through the furnace. The detector detects the light passed through the furnace. The camera captures an image of an inside of the furnace before performing a measurement process in which a sample is atomized in the furnace and its absorbance is measured. The captured image data storage unit stores the captured image data obtained by capturing the image by the camera in association with the measurement data corresponding to the captured image data.

3 Claims, 3 Drawing Sheets

ATOMIC ABSORPTION SPECTROPHOTOMETER

TECHNICAL FIELD

The present invention relates to an atomic absorption spectrophotometer use for a quantitative analysis of a metallic element.

BACKGROUND ART

As one of atomic absorption spectrophotometers, there is an atomic absorption spectrophotometer using a tube-like furnace made of graphite. In such an atomic absorption spectrophotometer, a sample is injected into a furnace from a small hole provided in the furnace using an instrument such as a syringe needle, and then the furnace is heated according to a predetermined temperature program to atomize the sample. At this time, measurement light from a light source composed of a hollow cathode lamp is irradiated in the furnace, passed through the atomic vapor, and the transmitted light is detected by a detector. Thus, the absorbance to a specific wavelength by the atomized sample component is measured (see Patent Document 1)

PRIOR ART

Patent Document

Patent Document 1: Japanese Unexamined Patent Application Publication No. 2004-325341

SUMMARY OF THE INVENTION

Problems to be Solved by the Invention

In the above-mentioned atomic absorption spectrophotometer, at the time of measuring an unknown sample, the optimum analysis condition of the sample is unknown. Therefore, there may sometimes occur bumping of the sample when raising the temperature of the furnace or injection failure of the sample into the furnace. In such a case, the user will know such abnormality from the dispersion of the measurement data, but since the cause cannot be confirmed afterwards. Therefore, it was necessary to again perform the investigation of the cause and the identification of the analysis condition, which took much labor and time.

In view of the above, the present invention aims to enable ex-post verification of a state in a furnace before measuring a sample.

Means for Solving the Problems

An atomic absorption spectrophotometer according to the present invention includes an atomization unit provided with a tube-like furnace and configured to atomize a sample injected into the furnace by heating the sample, a light source configured to emit light of a wavelength of a measurement target toward the atomization unit so that the light passes through the furnace, a detector configured to detect the light passed through the furnace, an optical system configured to guide the light of the wavelength of the measurement target among the light from the furnace to the detector, a camera configured to capture an image of an inside of the furnace before performing a measurement process in which the sample is atomized in the furnace to measure absorbance of an atomized sample, and a captured image data storage unit configured to store a captured image data obtained by capturing an image by the camera in association with measurement data corresponding to the captured image data.

By the way, the captured image data obtained by the camera is a video image, so a large storage area is required to store all data. However, when the measurement is performed normally, it is unnecessary to verify the processes, such as, e.g., a sample injection and a temperature rise, afterwards. Regardless of the unnecessity, storing all of the captured image data is useless.

Therefore, in the present invention, it is preferable to further include: a captured image data organization unit configured to determine whether or not the measurement data obtained by the detector in the measurement process is normal and delete the captured image data captured by the camera immediately before the measurement process on normal measurement data from the captured image data storage unit. By providing the captured image data organization unit described above, the captured image data which is not required to be verified by the user later is deleted from the captured image data storage unit, capable of suppressing accumulation of unnecessary captured image data in the captured image data storage unit, which in turn can secure an area for storing other data.

The captured image data organization unit may be configured to determine whether or not the measurement data is normal by comparing a preset threshold value with signal strength of the measurement data or a value calculated based on the signal strength of the measured data. By doing so, it is easy to determine whether or not the measurement data is normal. The "value calculated based on a signal strength" denotes, for example, in addition to the peak value of absorbance calculated based on a signal strength, a standard deviation value of absorbance in case of repeated measurements.

In the case of determining whether or not measurement data is normal based on the peak value of absorbance, when the peak value of absorbance falls below a threshold value, it is determined that the measurement data is abnormal. On the other hand, in the case of determining whether or not the measurement data is normal based on the standard deviation value, when the standard deviation value exceeds a predetermined threshold value, it is determined that the measurement data is abnormal.

As a further preferred embodiment of the present invention, it can be exemplified by the atomic absorption spectrophotometer further including: a camera drive mechanism configured to move the camera between an imaging position on an optical path of the light from the light source and a non-imaging position deviating from the optical path of the light from the light source; and an imaging control unit configured to control an operation of the camera and that of the camera drive mechanism so that the camera is arranged at the imaging position to capture an image of an inside of the furnace with the camera during a period of time from when the sample is injected into the furnace until the measurement process is performed and the camera is arranged at the non-imaging position when performing the measurement process. With this embodiment, image capturing in the furnace can be performed automatically.

Effects of the Invention

In the atomic absorption spectrophotometer according to the present invention, the atomic absorption spectrophotometer is provided with a captured image data storage unit configured to store a camera configured to capture an image of an inside of the furnace before performing a measurement process and a captured image data storage unit configured to store the captured image data in association with a measurement data obtained by the measurement process. Therefore, it is possible to perform verification as to whether or not the sample has been injected normally in the furnace or whether or not bumping of the sample has occurred afterwards after completion of the analysis.

EMBODIMENTS FOR CARRYING OUT THE INVENTION

Figure 1:
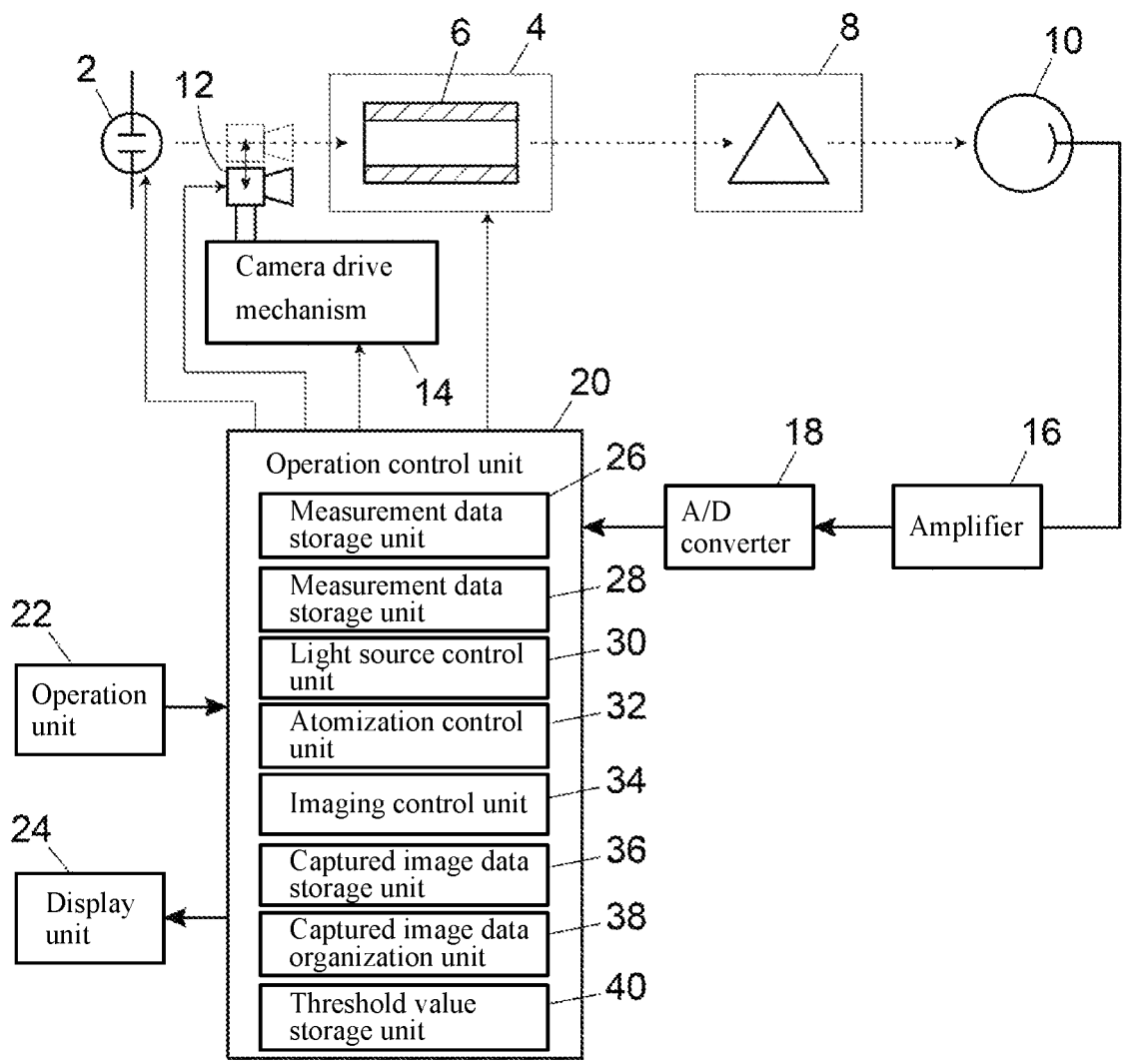
FIG. 1 is a block diagram schematically showing an embodiment of an atomic absorption spectrophotometer.

One embodiment of an atomic absorption spectrophotometer will be described with reference to FIG. 1.

The atomic absorption spectrophotometer of this embodiment is provided with a hollow cathode lamp 2 as a light source, an atomization unit 4, a spectroscope 8, a photomultiplier tube 10 as a detector, a camera 12, a camera drive mechanism 14, an amplifier 16, an analog/digital converter (A/D converter) 18, an operation control unit 20, an operation unit 22, and a display unit 24. Although not depicted, a suitable converging optical system is arranged between the hollow cathode lamp 2 and the atomization unit 4 and between the atomization unit 4 and the spectroscope 8.

The atomization unit 4 is provided with a graphite tube 6 as a furnace. A sample injection hole (not shown) is provided in the upper part of the graphite tube 6. The graphite tube 6 heats the sample to a high temperature to atomize it by applying a large current. The hollow cathode lamp 2 is provided at one end side of the graphite tube 6 and emits light including the emission line spectrum toward the graphite tube 6 so as to pass through the inside of the graphite tube 6.

The spectroscope 8 is provided with an inlet slit (not shown), a diffraction grating, and an outlet slit (not shown), and is configured to guide the light passed through the graphite tube 6 and incident from the inlet slit to the diffraction grating to diffract, emit the measurement light from the outlet slit, and guide it to the photomultiplier tube 10.

The camera 12 is moved by the camera drive mechanism 14 between the position on the optical path of the light traveling from the light source 2 to the graphite tube 6 (hereinafter, this position will be referred to as "imaging position") and the position deviated from the optical path (hereinafter, this position will be referred to as "non-imaging position"). The camera drive mechanism 14 is provided with an arm for holding and operating the camera 12. The cameral 12 is configured to be moved in accordance with the operation of the arm by driving a motor.

The electrical signal obtained by photoelectric conversion in the photomultiplier tube 10 is amplified by the amplifier 16, converted into a digital signal by the A/D converter 18, and then input into the operation control unit 20.

The operation unit 22 and the display unit 24 are electrically connected to the operation control unit 20. The user inputs information to the operation control unit 20 via the operation unit 22. The operation control unit 20 displays information, such as, e.g., measurement data, on the display unit 24. The operation control unit 20 is realized by a dedicated computer or a general-purpose personal computer.

The operation control unit 20 is provided with a measurement data processing unit 26, a measurement data storage unit 28, a light source control unit 30, an atomization control unit 32, an imaging control unit 34, a captured image data storage unit 36, a captured image data organization unit 38, and a threshold value storage unit 40. The measurement data processing unit 26, the measurement data storage unit 28, the light source control unit 30, the atomization control unit 32, the imaging control unit 34, and the captured image data organization unit 38 are functions obtained by executing a program stored in the storage area of the operation control unit 20 by an arithmetic device. The captured image data storage unit 36 and the threshold value storage unit 40 are functions realized by the storage area of the operation control unit 20.

The measurement data processing unit 26 processes the measurement data based on the signal from the photomultiplier tube 10 input to the operation control unit 20 via the amplifier 16 and the A/D converter 18. The processed measurement data is stored in the measurement data storage unit 28.

The light source control unit 30 makes the hollow cathode lamp 2 generate light of the wavelength used for the measurement by adjusting the voltage applied to the hollow cathode lamp 2.

The atomization control unit 32 is configured to cause the atomization unit 4 to execute a temperature rising operation, an ashing operation, and an atomization operation on the basis of a preset temperature program after the injection of the sample into the graphite tube 6. The temperature rising operation denotes an operation of gradually raising the temperature of the graphite tube 6 to a predetermined temperature (for example, 600° C.). The ashing operation denotes an operation of drying the sample by maintaining the temperature for a certain period of time after the temperature rising operation. The atomization operation denotes an operation for atomizing the sample by raising the temperature of the graphite tube 6 to a further high temperature (for example, 2,500° C.) after completion of the ashing operation.

The imaging control unit 34 is configured to control the image capturing operation of the camera 12 and the moving operation of the camera 12 by the camera drive mechanism 14. Specifically, from the stage of injecting the sample into the graphite tube 6, the camera 12 is arranged at the imaging position and starts image capturing of the inside of the graphite tube 6. The image capturing of the inside of the graphite tube 6 continues until completion of the ashing operation of the sample. Upon completion of ashing of the sample, the image capturing by the camera 12 is stopped and the camera 12 is moved to the non-imaging position. The captured image data in the graphite tube 6 acquired by the camera 12 is stored in the measurement captured image data storage unit 36 in a state associated with the measurement data of the absorbance of the sample which has been atomized and measured thereafter.

The captured image data organization unit 38 deletes unnecessary captured image data among the captured image data stored in the captured image data storage unit 36 after completion of the series of analysis operations. Whether or not the captured image data is unnecessary is determined based on whether or not the measurement data associated with the captured image data is normal. When the measurement data is normal, it is determined that the captured image data is unnecessary. The determination as to whether or not the measurement data is normal is made according to whether or not the peak value of absorbance in the measurement data or its standard deviation value exceeds the threshold value preset and stored in the threshold value storage unit 40. When the measurement data is normal, the captured image data becomes unnecessary since it is unnecessary to perform verification of presence or absence of injection failure of the sample or presence or absence of bumping of the sample.

As the threshold value for determining whether or not the measurement data is normal based on the standard deviation value, for example, the coefficient of variation CV of the repetition number calculated by the following equation can be used.

$$CV = 100 \times s/x_{avg}$$

Here, "s" is a sample standard deviation, and in the case of the iterative measurements of n times, it can be expressed as follow:

$$s = \sqrt{\sum_{i=1}^{n} (xi - x_{avg})^2 / (n-1)}$$

"$X_{avg}$" is an average value of the measured absorbance, and "$x_i$" is an absorbance value obtained in each measurement. In addition, as the threshold value, it is possible to use, for example, the absorption value by the background or the absorbance value itself.

The operation control unit 20 can display, in addition to the measurement data stored in the measurement data storage unit 28 after the arithmetic processing in the measurement data processing unit 26, the captured image data stored in the captured image data storage unit 36, on the display unit 24. The measurement data stored in the measurement data storage unit 28 and the captured image data stored in the captured image data storage unit 36 are associated with each other. When the user finds abnormal measurement data via the display unit 24, the captured image data concerning the measurement can be easily read from the captured image data storage unit 36 and reproduced.

Next, a series of operations of this atomic absorption spectrophotometer will be described with reference to the flowcharts shown in FIG. 2 and FIG. 3 together with FIG. 1.

First, a predetermined voltage is applied to the hollow cathode lamp 2 to generate measurement light. Before performing the injection operation of the sample, the camera 12 is arranged at the imaging position on the optical path of the light travelling from the hollow cathode lamp 2 to the graphite tube 6, and image capturing in the graphite tube 6 is started (Step S1). After that, the sample is injected into the graphite tube 6 (Step S2).

After injecting the sample, the temperature rising operation (Step S3) of the graphite tube 6 and the ashing operation of the sample (Step S4) are executed. At the timing when the ashing operation of sample is completed, the image capturing by the camera 12 is terminated and the camera 12 is moved to the non-measuring position (Step S5). By moving the camera 12 to the non-measuring position, the light from the hollow cathode lamp 2 blocked by the camera 12 passes through the graphite tube 6 and is guided to the photomultiplier tube 10. At this time, in the atomization unit 4, an atomization operation for atomizing the sample by further heating the graphite tube 6 to a higher temperature is performed. The light from the hollow cathode lamp 2 passes through the atomic vapor generated the atomization operation. The absorbance of the atomized sample is measured (Step S6). The process of measuring the absorbance of the atomized sample will be referred to as a measurement process.

After completion of the above-described measurement process, the measurement data obtained by the photomultiplier tube 10 and the captured image data obtained by the camera 12 are stored in the measurement data storage unit 28 and the captured image data storage unit 36 in a mutually associated manner. When there is a sample to be measured next, the above-described series of analysis operations for the sample are performed. After completion of measurements of all the samples, the captured image data stored in the captured image data storage unit 36 is organized (Step S9).

Figure 3:
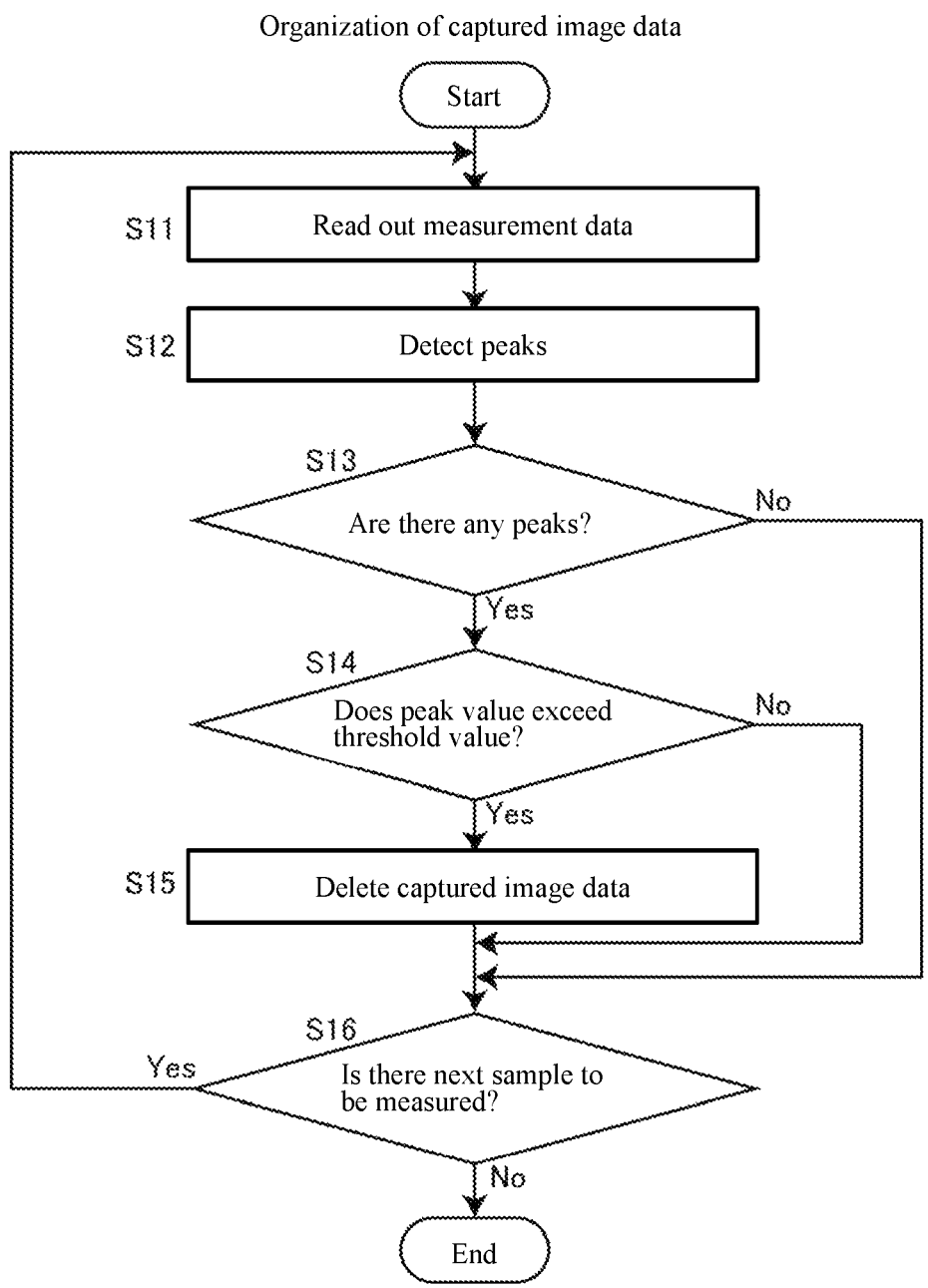
FIG. 3 is a flowchart showing an organizing operation of the captured image data of the embodiment.

As shown in FIG. 3, in organizing the captured image data, the measurement data stored in the measurement data storage unit 28 is first read out (Step S11), and the peak of absorbance of the sample is detected (Step S12).

In cases where no peak is detected from the measurement data, it is conceivable that the sample was not injected normally into the graphite tube 6, bumping of the sample occurred during the temperature rising operation and the sample was scattered, which is determined that the measurement data is not normal (Step S13). In this case, the corresponding captured image data associated with the measurement data is left in the captured image data storage unit 36 without being deleted.

Even if a peak is detected from the measurement data, in cases where its peak value falls below a preset threshold value, it is conceivable that sample injection failure in the graphite tube 6 occurred or sample bumping occurred during the temperature rising operation, which is determined that the measurement data is not normal (Steps S13 and S14). In this case as well, the corresponding captured image data associated with the measurement data is left in the captured image data storage unit 36 without being deleted.

As described above, the determination as to whether or not the measurement data is normal can be performed based on a standard deviation value. In the case of determining whether or not the measurement data is normal based on a standard deviation value, it is determined that the measurement data is abnormal when the standard deviation value exceeds a predetermined threshold value.

In cases where the peak value of the measurement data exceeds a threshold value, it is determined that the measurement data is normal (Step S14), and the captured image data associated with the measurement data is deleted from the captured image data storage unit 36. The above operation is performed for all data (Step S16), and unnecessary captured image data stored in the captured image data storage unit 36 is deleted.

Figure 2:
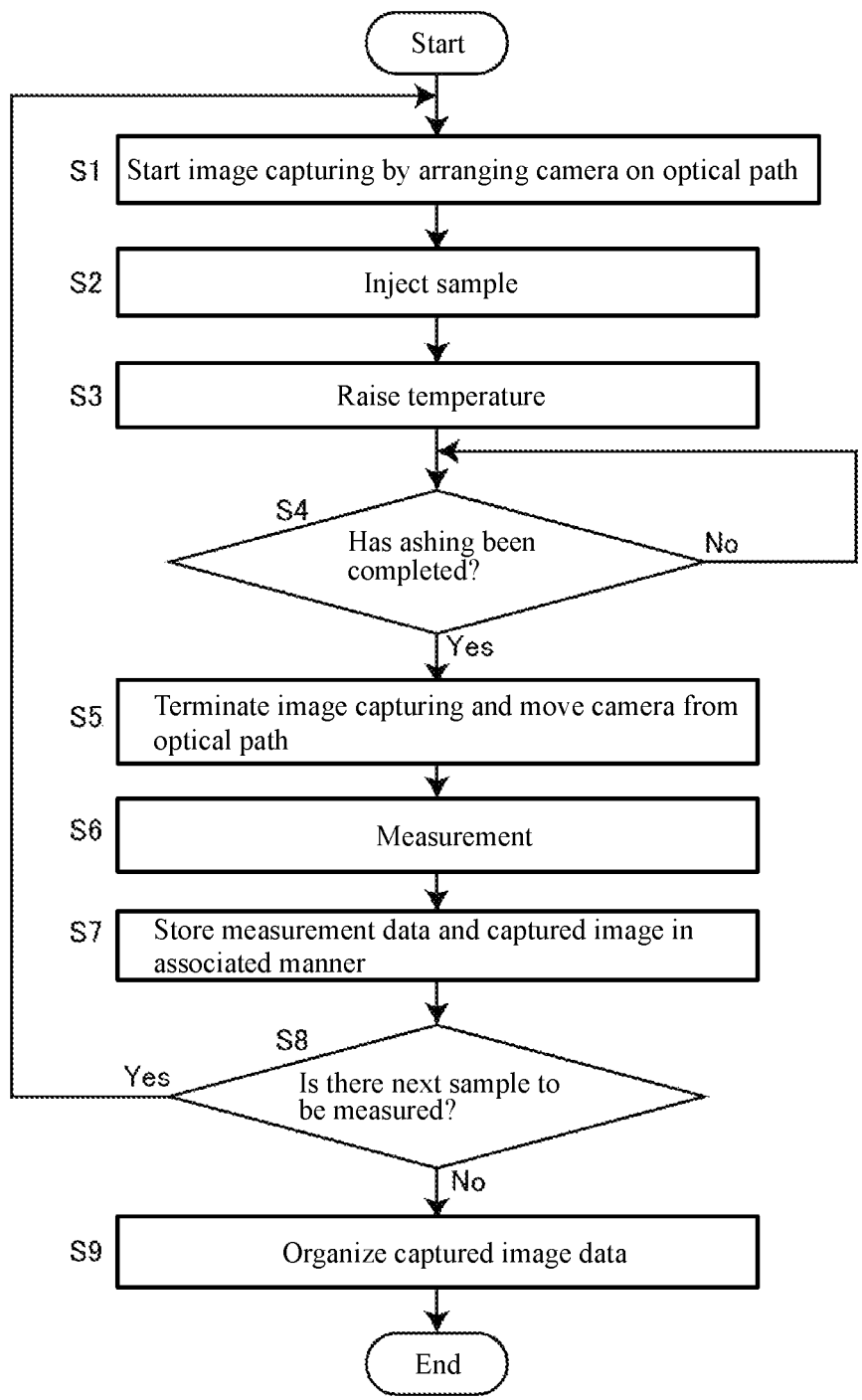
FIG. 2 is a flowchart showing an example of a measurement operation of the embodiment.

In the embodiment shown in FIG. 1, when capturing the image of the inside of the graphite tube 6, the camera 12 is arranged between the hollow cathode lamp 2 and the atomization unit 4 so as to directly capture the image of the inside of the graphite tube 6. However, the image capturing can be performed indirectly using a mirror.

Further, the camera 12 may be arranged between the atomization unit 4 and the spectroscope 8. In that case, in order to prevent that the image capturing by the camera 12 becomes impossible due to the light from the hollow cathode lamp 2, it may be configured such that at a timing when the camera 12 is arranged between the atomization unit 4 and the spectroscope 8, a shutter for shielding the light from the hollow cathode lamp 2 may be arranged between the hollow cathode lamp 2 and the atomization unit 4.

DESCRIPTION OF REFERENCE SYMBOLS

2 hollow cathode lamp
4 atomization unit
6 graphite tube
8 spectroscope
10 photomultiplier tube
12 camera
14 camera drive mechanism
16 amplifier
18 A/D converter
20 operation control unit
22 scanning unit
24 display unit
26 measurement data processing unit
28 measurement data storage unit
30 light source control unit
32 atomization control unit
34 imaging control unit
36 captured image data storage unit
38 captured image data organization unit
40 threshold storage unit

The invention claimed is:

1. An atomic absorption spectrophotometer, comprising:
   an atomization unit provided with a tube-like furnace and configured to atomize a sample injected into the furnace by heating the sample;
   a light source configured to emit light of a wavelength of a measurement target toward the atomization unit so that the light passes through the furnace;
   a detector configured to detect the light passed through the furnace;
   an optical system configured to guide the light of the wavelength of the measurement target among the light from the furnace to the detector;
   a camera configured to capture an image of an inside of the furnace before performing a measurement process in which the sample is atomized in the furnace to measure absorbance of an atomized sample;
   a measurement data storage unit configured to store a measurement data obtained by performing the measurement process;
   a captured image data storage unit configured to store a captured image data obtained by capturing an image by the camera in association with the measurement data which is stored by the measurement data storage unit and is corresponding to the captured image data; and
   a captured image data organization unit configured to determine whether or not the measurement data obtained by the detector in the measurement process is normal and delete the captured image data captured by the camera immediately before the measurement process on normal measurement data from the captured image data storage unit.

2. The atomic absorption spectrophotometer as recited in claim 1,
   wherein the captured image data organization unit is configured to determine whether or not the measurement data is normal by comparing a preset threshold value with a signal strength of the measurement data or a value calculated based on the signal strength of the measured data.

3. The atomic absorption spectrophotometer as recited in claim 1, further comprising:
   a camera drive mechanism configured to move the camera between an imaging position on an optical path of the light from the light source and a non-imaging position deviating from the optical path of the light from the light source; and
   an imaging control unit configured to control an operation of the camera and that of the camera drive mechanism so that the camera is arranged at the imaging position to capture an image of an inside of the furnace with the camera during a period of time from when the sample is injected into the furnace until the measurement process is performed and the camera is arranged at the non-imaging position when performing the measurement process.

* * * * *